US009730453B2

(12) United States Patent
Barazani

(10) Patent No.: US 9,730,453 B2
(45) Date of Patent: Aug. 15, 2017

(54) METHOD FOR CONTROLLING INSECTS IN PLANTS

(75) Inventor: Avner Barazani, Omer (IL)

(73) Assignee: MAKHTESHIM CHEMICAL WORKS LTD., Beer Sheva (IL)

(*) Notice: Subject to any disclaimer, the term of this patent is extended or adjusted under 35 U.S.C. 154(b) by 0 days.

(21) Appl. No.: 13/132,347

(22) PCT Filed: Dec. 16, 2009

(86) PCT No.: PCT/IL2009/001193
§ 371 (c)(1),
(2), (4) Date: Jul. 11, 2011

(87) PCT Pub. No.: WO2010/076782
PCT Pub. Date: Jul. 8, 2010

(65) Prior Publication Data
US 2011/0263655 A1    Oct. 27, 2011

Related U.S. Application Data

(60) Provisional application No. 61/141,749, filed on Dec. 31, 2008.

(51) Int. Cl.
| *A61K 31/44* | (2006.01) |
| *A01N 47/40* | (2006.01) |
| *A01N 43/40* | (2006.01) |
| *A01N 47/34* | (2006.01) |
| *A01N 47/36* | (2006.01) |
| *A01N 51/00* | (2006.01) |

(52) U.S. Cl.
CPC ............. *A01N 47/40* (2013.01); *A01N 43/40* (2013.01); *A01N 47/34* (2013.01); *A01N 47/36* (2013.01); *A01N 51/00* (2013.01)

(58) Field of Classification Search
None
See application file for complete search history.

(56) References Cited

U.S. PATENT DOCUMENTS

| 6,685,954 | B2 | 2/2004 | Jeannin |
| 2004/0053783 | A1 | 3/2004 | Kern |
| 2004/0078843 | A1 | 4/2004 | Kern |
| 2009/0156399 | A1 | 6/2009 | Hungenberg et al. |
| 2009/0298888 | A1 | 12/2009 | Thielert et al. |

FOREIGN PATENT DOCUMENTS

| CN | 1292218 | 4/2001 | |
| CN | 1299596 A | 6/2001 | |
| CN | 1308861 | 8/2001 | |
| CN | 1341360 | 3/2002 | |
| CN | 1399884 | 3/2003 | |
| CN | 1480040 | 3/2004 | |
| CN | 1650717 | 8/2005 | |
| CN | 1911024 | 2/2007 | |
| CN | 100353839 | 12/2007 | |
| CN | 101204156 | 6/2008 | |
| JP | 10324605 | 12/1998 | |
| WO | 9104965 A1 | 4/1991 | |
| WO | WO95/33380 A1 | 12/1995 | |
| WO | WO 99/18796 | * 4/1999 | ............. A01N 47/00 |
| WO | WO99/18796 A2 | 4/1999 | |
| WO | 9925188 A2 | 5/1999 | |
| WO | WO2005/053394 A2 | 6/2005 | |
| WO | WO 2006/048868 | * 5/2006 | ............. A01N 43/90 |
| WO | WO2006/048868 A2 | 5/2006 | |
| WO | WO2007/019962 A1 | 2/2007 | |
| WO | 2012017428 A2 | 2/2012 | |

OTHER PUBLICATIONS

Stansly et al (Proc Fla State Hort Soc 118:132-141, 2005).*
International Search Report and Written Opinion for PCT/IL2009/001193, mailed Mar. 1, 2011, 11 pages.
Bessin, Ric and Hartman, John, Extension Plant Pathologist, University of Kentucky Extension Service, College of Agriculture, ENTFACT-219 (2002), Revised Nov. 2003, 2 pages.
Utah State University Extension, Tree Fruit IPM advisory (Jun. 17, 2010), 6 pages.
Welty, Celeste and Murphy, Janet, Ohio State University Extension Fact Sheet, Woolly Apple Aphid, HYG-2208-94 (2000), 4 pages.
Mattos, Marco Antonio A., et al., "Agrochemica strategies evaluation for the control of Bemisia argentifolii Bellows & Perring on tomatoes", Pesticidas (2002), 12, 131-144 (English abstract only).
Hemiptera Suborder Homoptera; ENT 425; General Entomology; Resource Library; Compendium; 2 pages, Jan. 5, 2014.
JP 2003055118 A with English Abstract; Date of Publication: Feb. 26, 2003; 7 pages, Abstract only.
Beers et al.; "Biology and management of woolly apple aphid, *Eriosoma lanigerum* (Hausmann), in Washington state"; Pome Fruit Arthropods; 1OBC/wprs Bulletin vol. 30 (4); 2007; pp. 37-42.
Lawrence I. Gilbert et al., Eds, Insect control, Biological and synthetic agents, 2010, pp. 61-90, 104-113, 151-181.
Simon-Delso et al. Systemic insecticides (neonicotinoids and fipronil): trends, uses, mode of action and metabolites. Environ Sci Pollut Res 2015, vol. 22, pp. 5-34.
U.S. Appl. No. 11/718,591, filed Jan. 12, 2016 Response to Final Office Action (28 pages).
U.S. Appl. No. 11/718,591 Final Office Action dated Aug. 13, 2015 (19 pages).
Van Ered et al., Pesticide metabolism in plants and microorganisms, Weed Science, 2003, vol. 51, pp. 472-495.
Alston et al. "Apple Aphids", published by Utah State University Cooperative Extension, ENT-143-98, Oct. 2010, 7 pages.

(Continued)

*Primary Examiner* — Craig Ricci
(74) *Attorney, Agent, or Firm* — Cantor Colburn LLP

(57) ABSTRACT

The invention relates to a method for controlling woolly apple aphid insect comprising contacting the insect or a locus, where control of the insect is desired, with a combination of at least one neonicotinoid compound and at least one benzoylphenyl urea compound.

10 Claims, No Drawings

(56) References Cited

OTHER PUBLICATIONS

Beers et al. "Woolly Apple Aphid Control", Proceedings of the 76th Annual Western Orchard Pest & Disease Management Conference published by Washington State University, Jan. 9-11, 2002, 4 pages.
Gontijo et al. "Natural Enemies of Woolly Apple Aphid (Hemiptera: Aphididae) in Washington State", Enviromental Entomology, vol. 41(6), 2012, pp. 1364-1371.
Gupta et al. "Management and Comparative Efficacy of Various Treatments Against *Eriosoma lanigerum* Hausmann on Apple Trees (*Malus domestica borkh.*) in Jammu Province of Jammu & Kashmir State", International Journal of Advanced Biological Research, vol. 5(4), 2015, pp. 319-321.
Lordan et al. "Woolly apple aphid *Eriosoma lanigerum* Hausmann ecology and its relationship with climatic variables and natural enemies in Mediterranean areas"; Bulletin of Entomological Research, 2015, vol. 105, pp. 60-69.
Vea et al. "Aphid Efficacy: A Literature Review", IR-4 Ornamental Horticulture Program, Aug. 20, 2015, 73 pages.

\* cited by examiner

METHOD FOR CONTROLLING INSECTS IN PLANTS

FIELD OF THE INVENTION

The invention relates to the field of insecticidal compositions for controlling insects in plants, especially fruit trees.

BACKGROUND OF THE INVENTION

In the practice of pest control, particularly insect control, there are two main factors which determine the effectiveness of the treatment: 1) the immediate action on the pests (known in the art as "knock-down action"); and 2) the long term action (known also as "residual action"). Effective knock-down insecticides include pyrethroids, organic phosphoric acid esters, neonicotinoids such as for example, imidacloprid, acetamiprid and phenyl pyrazoles (fipronil). Effective long term insecticides include insect growth regulators (IGR) of various types, e.g. chitin synthesis inhibitors. Current methods for achieving the desired effect include repeated treatments over time with insecticides which have an effective knock-down action. The disadvantages of repeated treatments are: a) the use of relatively large doses of insecticides over time, which may cause environmental hazards; and b) there are certain periods within the life cycle of the crop when treatments with effective knock-down insecticides are prohibited since they may be absorbed in the crop and/or may damage the crop. On the other hand, using long term active insecticides may aid in preventing repeated treatments, but may not be effective against certain insects which have reached a certain developmental stage in their life cycle. For example, the group of insecticides known as insect growth regulators (IGR), which generally have effective long term action, are almost ineffective against adult insects due to their low knock-down effect.

Combination treatments of knock-down and long term insecticides have been reported. U.S. Pat. No. 6,685,954 reports on the effectiveness of fipronil in combination with IGR of the juvenile hormone mimic group in the treatment of ectoparasites in mammals.

Insecticidal combinations are also described in WO2006/048868, WO99/18796 and WO95/33380.

The woolly apple aphid, *Eriosoma lanigerum*, is one of several species of aphids that can infest apple trees. Other aphid species found on apple trees are rosy apple aphid and green apple aphid. Such aphids may be found either in commercial orchards or in home plantings. Woolly apple aphid feeds mainly on apple, but may be found also on elm, pear, quince, hawthorn, mountain ash, and cotoneaster.

Woolly apple aphid is an indirect pest (insect) that weakens the tree by its feeding on bark and roots, which reduces tree health, prevents wounds from healing, and transmits perennial apple canker. Woolly apple aphid is also a direct pest when it infests fruit cores of some cultivars.

An insecticide can be applied if woolly apple aphid is detected at damaging levels on above-ground parts of trees. Insecticides are most effective if applied when the aphid is in the active crawler stage and is just moving up into the tree. This may occur in late-spring or not until mid-summer. Thorough coverage of the canopy is needed for the insecticide to be effective. Due to the aphids' waxy covering, high volume application is needed to get thorough spray coverage. A second application may be needed two weeks after the first if aphids continue to be detected.

Insecticides used to control woolly apple aphid are dimethoate (Cygon), endosulfan (Thiodan), chlorpyrifos (Lorsban), or methyl parathion (Penncap-M). These are contact insecticides from chemical groups which are not recommended because of their toxicological profile, some of them already banned. Also, with the time their efficacy was decreased.

Thus, although there are several treatments known in the art for controlling woolly apple aphids, those treatments are insufficient and/or they are considered toxicological.

A pesticide composition comprising imidacloprid and chlorpyrifos for control of apple aphid has been reported in CN1299596A.

It will be highly advantageous to have a new effective method for controlling woolly apple aphid.

There is a long felt need for an effective method of treating woolly apple aphid having reduced environmental, toxic and ecotoxic problems.

It is therefore a purpose of the invention to provide a method and composition for effective control of woolly apple aphid insect useful for plant protection, especially for controlling insect infested fruit trees, such as apple trees.

SUMMARY OF THE INVENTION

The invention relates to a method for controlling woolly apple aphid insect comprising contacting the insect or a locus, where control of the insect is desired, with a combination of at least one neonicotinoid compound and at least one benzoylphenyl urea (BPU) compound.

The invention further relates to a method of controlling insect infestation of a plant, wherein the insect is woolly apple aphid, comprising contacting one or both of the plant and its environment with a combination of at least one neonicotinoid compound and at least one benzoylphenyl urea (BPU).

The invention additionally relates to a composition comprising a combination of at least one neonicotinoid compound and at least one benzoylphenyl urea (BPU) compound, for controlling woolly apple aphid.

The invention further relates to use of a combination of at least one neonicotinoid compound and at least one benzoylphenyl urea (BPU) compound for controlling woolly apple aphid.

Additionally, the invention relates to a kit comprising (a) at least one container including at least one neonicotinoid compound; (b) at least one container including at least one benzoylphenyl urea compound; and instructions for applying a combination of the neonicotinoid compound and the benzoylphenyl urea compound onto woolly apple aphid insect or a locus where control of the insect is desired.

Moreover, the invention relates to a kit comprising at least one container including a combination of at least one neonicotinoid compound and at least one benzoylphenyl urea compound, and instructions for applying the combination onto woolly apple aphid insect or a locus where control of the insect is desired.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

The invention relates to a method for controlling woolly apple aphid insect comprising contacting the insect or a locus, where control of the insect is desired, with a combination of at least one neonicotinoid compound and at least one benzoylphenyl urea (BPU) compound.

As used herein the term "controlling" covers both treatment and prevention.

As used herein, the term "controlling insect", "controlling woolly apple aphid", "an insect control agent" and similar terms refer to the ability of the combination of compounds of the invention to have a detrimental effect on the insect such as by preventing, combating, eradicating, destroying, repelling insects, increasing the mortality, inhibiting or reducing the growth and/or development of insects.

As used herein, the term "controlling insect", "controlling woolly apple aphid", "an insect control agent" and similar terms also refers to the ability of the combination of compounds to control e.g. the behavior, physiology, or biochemical site or process of an insect by causing a harmful effect on the insect including, for example but without limitation, physiological damage to the insect; inhibition or modulation of insect growth; inhibition or modulation of insect reproduction; inhibition or complete deterrence of insect movement into a locus; initiation or promotion of insect movement away from a locus; inhibition or complete suppression of insect feeding activity; or death of the insect. An insect control agent may be considered an "insecticide" if it kills at least one individual in an insect population. Additionally, an insect control agent may be non-lethal at a particular concentration or amount (such as a deterrent of insect) and an insecticide at a different concentration or amount.

The efficacy of the subject compounds or compositions may be determined from their effect on the insect population (e.g. by affecting an insect's behavior, physiology, or biochemical site or process), including (but not limited to) physiological damage to an insect, inhibition or modulation of insect growth, inhibition or modulation of insect reproduction by slowing or arresting proliferation, inhibition or complete deterrence of insect movement into a locus, initiation or promotion of insect movement away from a locus, inhibition or elimination of insect feeding activity, or death of the insect, all of which are encompassed by the term "controlling". Thus, a compound or composition that controls an insect (i.e., an insect control agent) affects its presence, development, behavior, and/or physiological condition at a locus.

As used herein, the term "woolly apple aphid insect" or "woolly apple aphid" refers to a woolly apple aphid at any of its developmental stages, including eggs, nymphs, larva, adult or any other form during its life cycle. The compounds and the composition of the invention, may be used against all the woolly apple aphid insect developmental stages including winged and wingless individuals, at any desirable locus and at any season of the year.

Efficacy of a compound may be assessed by treating a plant and/or environmental locus with the compounds or compositions described herein and observing the effects on the infesting insect population and/or host plant. The efficacy of the compounds or compositions may be monitored by examining the state of the infested host and/or environmental locus infestation by the insect population before and after application of a compound or composition in light of physiological damage to a plant host caused by the insect infestation. The efficacy may be also assessed by examining the existence, state and/or the size of the woolly apple aphid's colonies at particular plant organs.

The term "physiological damage to a plant" refers to the damage that is caused to the tree: Woolly apple aphid is a serious pest of apples, particularly young trees because they suck the tree's roots and sprouts and cause swelling and galls formation. As the woolly apple aphid populations grow, aphids are commonly found on sprouts in the center of the tree. The tree will begin to swell and form galls at the feeding sites. As the number of aphids on the above ground portion of the tree increase, they may move down to the roots and trunk below ground surface. Their feeding on the roots produces the greatest damage especially to young trees. The root systems can be damaged, which may lead to the tree's death. Such trees often have short fibrous roots, which may result in uprooting. Further, fungi can attack the damaged roots. Aphid feeding on the root systems also disrupts the nutrient balance of root tissue, which can affect growth of other parts of the tree.

According to certain embodiments the combination of compounds may be synergistic. A synergistic effect of a combination of compounds is present when the activity of the active compound combinations exceeds the total of the activities of the active compounds when applied individually. The expected activity for a given combination of active compounds can be calculated by the Colby's formula (S. R. Colby, Weeds 15 (1967), 20-22) and compared to the observed efficacies. If the observed response of the combination is greater than the expected (or predicted) response then the combination is said to be synergistic.

The term "contacting", as used herein, refers to applying the compounds and compositions of the invention to the insect, to a site of infestation by an insect, a potential site of infestation by the insect, which may require protection from infestation, or the environment around the habitat or potential habitat of the insect. The application may be by methods described in the present invention such as by spraying, dipping, etc.

As used herein the term "plant" includes reference to whole plants, plant organs (e.g. leaves, stems, twigs, roots, trunks, limbs, shoots, fruits etc.), or plant cells. This term also encompasses plant crops such as fruits. Preferably, the plant is a tree or shrub, more preferably a fruit tree (e.g. an apple tree, an elm tree, a pear tree, a quince tree, a hawthorn tree, a mountain ash tree, and cotoneaster tree).

Throughout the description, percentages of components are by weight, unless specifically noted differently. The terms "benzoyl urea", "benzoylphenyl urea" and "BPU", as used throughout the specification, are synonymous.

It has surprisingly been found, in experiments conducted in apple trees at different locations, that the combination of at least one neonicotinoid compound and at least one benzoylphenyl urea (BPU) compound provides an effective control of woolly apple aphid.

BPU belongs to the long term IGR, group of insecticides and includes, for example without being limited, novaluron, lufenuron, hexaflumuron, triflumuron, diflubenzuron, chlorfluazuron, flufenoxuron, noviflumuron, teflubenzuron, flucycloxuron, or mixtures thereof.

Neonicotinoid is an example of a "knock-down" insecticide and includes, for example, without being limited, imidacloprid, acetamiprid, thiamethoxam, thiacloprid, nitenpyram, dinotefuran, clothianidin, or mixtures thereof.

According to a specific embodiment of the present invention the locus is one or both of a plant and its environment.

According to an embodiment of the invention, the plant is a fruit tree.

According to an embodiment of the invention the fruit tree may be selected from an apple tree, an elm tree, a pear tree, a quince tree, a hawthorn tree, a mountain ash tree, and cotoneaster tree. The fruit tree may be any other crop attacked by this insect.

According to a specific embodiment the fruit tree is an apple tree.

In an embodiment of the invention, the combination for controlling the woolly apple aphid insect comprises novaluron and acetamiprid.

In some embodiments, the BPU compound is selected from novaluron, lufenuron, hexaflumuron, triflumuron, diflubenzuron, chlorfluazuron, flufenoxuron, noviflumuron, teflubenzuron, flucycloxuron, and any combination thereof.

In some embodiments, the neonicotinoid compound is selected from imidacloprid, acetamiprid, thiamethoxam, thiacloprid, nitenpyram, dinotefuran, clothianidin, and any combination thereof.

According to certain embodiments the BPU compound is lufenuron.

According to certain embodiments the BPU compound is novaluron.

According to certain embodiments the BPU compound is flufenuxoron.

According to certain embodiments the BPU compound is selected from novaluron, lufenuron, flufenuxoron, and mixtures thereof.

According to certain embodiments the BPU compound is selected from novaluron, lufenuron, and mixtures thereof.

According to certain embodiments the BPU compound is selected from novaluron, flufenuxoron, and mixtures thereof.

According to certain embodiments the BPU compound is selected from lufenuron, flufenuxoron, and mixtures thereof.

According to certain embodiments the neonicotenoid compound is selected from imidacloprid, acetamiprid, thiamethoxam, thiacloprid, and mixtures thereof.

According to certain embodiments the neonicotenoid compound is imidacloprid

According to certain embodiments the neonicotenoid compound is acetamiprid.

According to certain embodiments the neonicotenoid compound is thiamethoxam.

According to certain embodiments the neonicotenoid compound is thiacloprid.

According to certain embodiments the neonicotenoid compound is selected from imidacloprid, acetamiprid, and mixtures thereof.

According to certain embodiments the neonicotenoid compound is selected from imidacloprid, thiamethoxam, and mixtures thereof.

According to certain embodiments the neonicotenoid compound is selected from imidacloprid, thiacloprid, and mixtures thereof.

According to certain embodiments the neonicotenoid compound is selected from acetamiprid, thiamethoxam, and mixtures thereof.

According to certain embodiments the neonicotenoid compound is selected from acetamiprid, thiacloprid, and mixtures thereof.

According to certain embodiments the neonicotenoid compound is selected from thiamethoxam, thiacloprid, and mixtures thereof.

According to certain embodiments the neonicotenoid compound is selected from imidacloprid, acetamiprid, thiamethoxam, and mixtures thereof.

According to certain embodiments the neonicotenoid compound is selected from imidacloprid, thiamethoxam, thiacloprid, and mixtures thereof.

According to certain embodiments the neonicotenoid compound is selected from imidacloprid, acetamiprid, thiacloprid, and mixtures thereof.

According to certain embodiments the neonicotenoid compound is selected from acetamiprid, thiamethoxam, thiacloprid, and mixtures thereof.

The combination may include any combination of the above neonicotenoid and BPU compounds, i.e., of individual compounds and of any sub-group combination. For example, if a number of different neonicotenoid and BPU compounds are disclosed and discussed, each and every combination of the neonicotenoid and BPU compounds are specifically contemplated. Thus, if a combination of (a) neonicotenoid compounds e.g. A, B, C, or mixtures thereof; and (b) BPU compounds e.g. D, E, F, or mixtures thereof is disclosed, then even if each is not individually recited, each compound is individually and collectively contemplated. Thus, each of the combinations A-D, A-E, A-F, B-D, B-E, B-F, C-D, C-E, and C-F are specifically contemplated and should be considered disclosed from disclosure of (a) A, B, C, or mixtures thereof; and (b) D, E, F, or mixtures thereof. Likewise, any subset or combination of these is also specifically contemplated and disclosed. Thus, for example, the sub-group of (a) A; and (b) D, E, F, or mixtures thereof are specifically contemplated and should be considered disclosed from disclosure of a combination of (a) A, B, C, or mixtures thereof; and (b) D, E, F, or mixtures thereof.

In some embodiments, the neonicotinoid compound and the benzoylphenyl urea (BPU) compound are administered sequentially or simultaneously (concomitantly).

The term "administered sequentially" means the successive administration of a dosage form including a first compound of the invention (i.e. one of a neonicotinoid and benzoylphenyl urea), and then administration of a dosage form of a second compound, which is different than the first compound, according to the embodiments of the invention. When administered sequentially the neonicotinoid compound and the benzoylphenyl urea compound are included in separate compositions.

If the neonicotinoid and the benzoylphenyl urea (BPU) compounds are administered sequentially, the order of administering thereof may be interchangeable.

The term "administered concomitantly" or "administered simultaneously" means administering the compounds substantially concurrently. These terms encompasses not only administering the two compounds in a single formulation but also the administration of each compound in its own separate formulation. Where separate formulations are used, the compounds can be administered at essentially the same time, i.e., concurrently.

In one embodiment of the invention the neonicotinoid compound and the benzoylphenyl urea (BPU) compound are administered within a time difference of not more than 14 days.

In another embodiment of the invention, the time difference between the administrations is not more than 10 days.

In another embodiment of the invention, the time difference between the administrations is not more than 5 days.

In another embodiment of the invention, the time difference between the administrations is about one day.

In an embodiment of the invention, the neonicotinoid compound and the benzoylphenyl urea (BPU) compound are applied in a single composition comprising thereof.

In another embodiment of the invention, the neonicotinoid compound and the benzoylphenyl urea (BPU) compound are applied in separate compositions comprising thereof.

Unless otherwise indicated, whenever a ratio, concentration, application rate, etc. of the neonicotinoid and benzoylphenyl urea (BPU) compounds are indicated it encompass both the case where such compounds are included in a single dosage form and the case where such compounds are included in separate dosage forms.

In an embodiment of the invention, the weight ratio of the neonicotinoid compound and the benzoylphenyl urea (BPU) compound is between 1:0.01 to 1:100.

In an embodiment of the invention, the weight ratio of the neonicotinoid compound and the benzoylphenyl urea (BPU) compound is between 1:0.02 to 1:50.

In an embodiment of the invention, the weight ratio of the neonicotinoid compound and the benzoylphenyl urea (BPU) compound is between 1:0.1 to 1:10.

In an embodiment of the invention, the weight ratio of the neonicotinoid compound and the benzoylphenyl urea (BPU) compound is between 1:1 to 1:6.

In an embodiment of the invention, the weight ratio of the neonicotinoid compound and the benzoylphenyl urea (BPU) compound is between 1:1.5 to 1:5.

In an embodiment of the invention, the weight ratio of the neonicotinoid compound and the benzoylphenyl urea (BPU) compound is between 1:1.5 to 1:4.

In an embodiment of the invention, the weight ratio of the neonicotinoid compound and the benzoylphenyl urea (BPU) compound is between 1:1.5 to 1:3.

In an embodiment of the invention, the weight ratio of the neonicotinoid compound and the benzoylphenyl urea (BPU) compound is between 1:1.5 to 1:2.

In an embodiment of the invention, the weight ratio of the neonicotinoid compound and the benzoylphenyl urea (BPU) compound is between 1:1.8 to 1:3.

In another embodiment of the invention, the weight ratio of the neonicotinoid compound and the benzoylphenyl urea (BPU) compound is about 1:2.

In another embodiment of the invention, the weight ratio of the neonicotinoid compound and the benzoylphenyl urea (BPU) compound is about 1:2.5.

In another embodiment of the invention, the weight ratio of the neonicotinoid compound and the benzoylphenyl urea (BPU) compound is 1:1.875.

By the term "about" it is meant ±20%.

In an embodiment of the invention, the amount of the neonicotinoid compound and the benzoylphenyl urea (BPU) compound is calculated to be equivalent to 1 to 6 g and 2 to 15 g, respectively, in 100 liter.

In an embodiment of the invention, the amount of the neonicotinoid compound and the benzoylphenyl urea (BPU) compound is calculated to be equivalent to 2 to 6 g and 5 to 10 g, respectively, in 100 liter.

In an embodiment of the invention, the amount of the neonicotinoid compound and the benzoylphenyl urea (BPU) compound is calculated to be equivalent to 2.5 g and 5 to 10 g, respectively, in 100 liter.

In an embodiment of the invention, the amount of the neonicotinoid compound and the benzoylphenyl urea (BPU) compound is calculated to be equivalent to 2.5 g and 10 g, respectively, in 100 liter.

In another embodiment of the invention, the amount of the neonicotinoid compound and the benzoylphenyl urea (BPU) compound is calculated to be equivalent to 2.5 g and 7.5 g, respectively, in 100 liter.

In another embodiment of the invention, the amount of the neonicotinoid compound and the benzoylphenyl urea (BPU) compound is calculated to be equivalent to 2.5 g and 5.0 g, respectively, in 100 liter.

In another embodiment of the invention, the amount of the neonicotinoid compound is calculated to be equivalent to 3 to 6 g and the benzoylphenyl urea (BPU) compound is between 1 to 15 g in 100 liter.

In another embodiment of the invention, the amount of the neonicotinoid compound is calculated to be equivalent to 4 g and the benzoylphenyl urea (BPU) compound is between 5 to 10 g in 100 liter.

In another embodiment of the invention, the amount of the neonicotinoid compound and the benzoylphenyl urea (BPU) compound is calculated to be equivalent to 4 g and 5 g, respectively, in 100 liter.

In another embodiment of the invention, the amount of the neonicotinoid compound and the benzoylphenyl urea (BPU) compound is calculated to be equivalent to 4 g and 7.5 g, respectively, in 100 liter.

In another embodiment of the invention, the amount of the neonicotinoid compound and the benzoylphenyl urea (BPU) compound is calculated to be equivalent to 4 g and 10 g, respectively, in 100 liter.

By the term "equivalent" is meant for example that an amount of X g and Y g of neonicotinoid compound and the BPU compound respectively, in 100 L is equivalent to an amount of 20X g and 20Y g of neonicotinoid compound and the BPU compound respectively, in 2000 L.

Thus, for example an amount of 4 g and 10 g of the neonicotinoid compound and the BPU compound respectively, in 100 liter are equivalent to 80 g and 200 g of the neonicotinoid compound and the BPU compound respectively, in 2000 liter.

The application rate expressed in volume/hectare may be as described herein below.

When applied to a plant, the application rate may be as indicated below with respect to fruit trees.

In an embodiment of the invention, when applied to fruit trees, the neonicotinoid compound is applied at a rate of 20 g/hectare to 500 g/hectare and the benzoylphenyl urea (BPU) compound is applied at a rate of 20 g/hectare to 500 g/hectare.

In an embodiment of the invention, when applied to fruit trees, the neonicotinoid compound is applied at a rate of 20 g/hectare to 100 g/hectare and the benzoylphenyl urea (BPU) compound is applied at a rate of 50 g/hectare to 250 g/hectare.

In an embodiment of the invention, when applied to fruit trees, the neonicotinoid compound is applied at a rate of 50 g/hectare to 80 g/hectare and the benzoylphenyl urea (BPU) compound is applied at a rate of 100 g/hectare to 220 g/hectare.

In an embodiment of the invention, when applied to fruit trees, the neonicotinoid compound is applied at a rate of 20 g/hectare to 120 g/hectare and the benzoylphenyl urea (BPU) compound is applied at a rate of 40 g/hectare to 300 g/hectare.

In an embodiment of the invention, when applied to fruit trees, the neonicotinoid compound is applied at a rate of 40 g/hectare to 80 g/hectare and the benzoylphenyl urea (BPU) compound is applied at a rate of 100 g/hectare to 200 g/hectare.

In an embodiment of the invention, when applied to fruit trees, the neonicotinoid compound is applied at a rate of 80 g/hectare to 100 g/hectare and the benzoylphenyl urea (BPU) compound is applied at a rate of 100 g/hectare to 200 g/hectare.

In an embodiment of the invention, when applied to fruit trees, the neonicotinoid compound is applied at a rate of 60 g/hectare to 100 g/hectare and the benzoylphenyl urea (BPU) compound is applied at a rate of 120 g/hectare to 250 g/hectare.

In an embodiment of the invention, when applied to fruit trees, the neonicotinoid compound is applied at a rate of 60 g/hectare to 100 g/hectare and the benzoylphenyl urea (BPU) compound is applied at a rate of 140 g/hectare to 220 g/hectare.

In an embodiment of the invention, when applied to fruit trees, the neonicotinoid compound is applied at a rate of 60 g/hectare to 100 g/hectare and the benzoylphenyl urea (BPU) compound is applied at a rate of 150 g/hectare to 200 g/hectare.

In an embodiment of the invention, when applied to fruit trees, the neonicotinoid compound is applied at a rate of about 80 g/hectare and the benzoylphenyl urea (BPU) compound is applied at a rate of 120 g/hectare to 250 g/hectare.

In an embodiment of the invention, when applied to fruit trees, the neonicotinoid compound is applied at a rate of about 80 g/hectare and the benzoylphenyl urea (BPU) compound is applied at a rate of 140 g/hectare to 220 g/hectare.

In an embodiment of the invention, when applied to fruit trees, the neonicotinoid compound is applied at a rate of about 80 g/hectare and the benzoylphenyl urea (BPU) compound is applied at a rate of 150 g/hectare to 200 g/hectare.

In another embodiment of the invention, the neonicotinoid compound is applied at a rate of 100 g/hectare to 350 g/hectare and the benzoylphenyl urea (BPU) compound is applied at a rate of 30 g/hectare to 100 g/hectare.

The BPU compound may be applied at a rate of 20 g/hectare to 500 g/hectare, 30 g/hectare to 500 g/hectare, 50 g/hectare to 500 g/hectare, 80 g/hectare to 500 g/hectare, 100 g/hectare to 500 g/hectare, 120 g/hectare to 500 g/hectare, 120 g/hectare to 350 g/hectare, 120 g/hectare to 250 g/hectare, or 140 g/hectare to 250 g/hectare.

The neonicotinoid compound may be applied at a rate of 20 g/hectare to 500 g/hectare, 30 g/hectare to 500 g/hectare, 30 g/hectare to 350 g/hectare, 60 g/hectare to 500 g/hectare, 60 g/hectare to 350 g/hectare, 60 g/hectare to 250 g/hectare, 60 g/hectare to 200 g/hectare, 60 g/hectare to 150 g/hectare, 60 g/hectare to 120 g/hectare, or 60 g/hectare to 100 g/hectare.

The BPU and neonicotinoid compounds may be applied according to any of combination of the above application rates.

In an embodiment of the invention, the application rate expressed in volume/ha may be in the range 200 to 3000 liter/ha. In a specific embodiment the application rate expressed in volume/ha may be in the range 800-2500 liter/ha. In a more specific embodiment the application rate expressed in volume/ha may be in the range 800-2000 liter/ha.

Preferably, the application rate expressed in volume/ha is about 2000 liter/ha.

As used herein "ha" refers to hectare.

The application volume refers to the volume of the diluted composition (e.g. spraying volume of the water-diluted composition).

Preferably the compounds of the invention are applied or administered by way of a composition comprising thereof.

In order to apply the combination of compounds of the present invention to an insect or a locus of an insect (e.g. plant susceptible to attack by an insect, to the soil or any other growth medium) the compounds are usually formulated with an inert diluent or carrier.

Typically, the compounds are mixed with a solid carrier, a liquid carrier, or gas carrier, optionally together with a surfactant or other additives useful for such formulations.

In an embodiment of the invention, the compositions comprise 0.0001 to 99% by weight of the compounds. In an embodiment of the invention, the compositions comprise 0.0001 to 95% by weight of the compounds. The compositions may comprise, for example, 1 to 85% by weight of the compounds. In a specific embodiment of the invention, the compositions comprise 5 to 60% of the compounds. If necessary the compositions may be diluted prior to use using a suitable diluent. The concentrations above refer to the case where the compounds are included in a single or separate compositions.

In an embodiment of the invention, the compounds may be included in a composition that is formulated in a manner which suits the specific application. Non-limiting examples of suitable formulations are; emulsifiable concentrates (EC), emulsions, oil in water (EW), suspension concentrates (SC), suspo-emulsions (SE), water dispersible granules (WG), capsule suspension (CS), soluble powders (SP), and wettable powders (WP).

The compositions of the invention may be prepared by methods well known to those skilled in the art, e.g. by means of conventional mixing, dissolving, pulverizing, granulating, compressing, emulsifying, etc. processes. See generally, Alan Knowles, Agrow Reports, New Developments in Crop Protection Product Formulation, 2005.

In a specific embodiment, the compositions may be diluted prior to use with a liquid diluent, preferably an aqueous diluent, preferably water. In a specific embodiment, the concentration of the active ingredients (neonicotinoid compound, BPU compound, or combination thereof) in the diluted composition (compositions diluted prior to use) may be in the range 0.0005-0.10% w/v, 0.001-0.10% w/v, 0.001-0.05% w/v, 0.001-0.03% w/v, 0.001-0.02% w/v, or 0.001-0.015% w/v.

In a specific embodiment, the concentration of the neonicotinoid compound in the diluted composition is in the range 0.001-0.012% w/v.

In a specific embodiment, the concentration of the neonicotinoid compound in the diluted composition is in the range 0.001-0.006% w/v.

In a specific embodiment, the concentration of the neonicotinoid compound in the diluted composition is in the range 0.002-0.006% w/v. In a specific embodiment, the concentration of the neonicotinoid compound in the diluted composition is in the range 0.003-0.005% w/v.

In a specific embodiment, the concentration of the BPU compound in the diluted composition is in the range 0.002-0.03% w/v.

In a specific embodiment, the concentration of the BPU compound in the diluted composition is in the range 0.002-0.015% w/v.

In a specific embodiment, the concentration of the BPU compound in the diluted composition is in the range 0.004-0.012% w/v. In a specific embodiment, the concentration of the BPU compound in the diluted composition is in the range 0.006-0.012% w/v. In a specific embodiment, the concentration of the BPU compound in the diluted composition is in the range 0.007-0.011% w/v.

The compounds may be applied by any of the known means of applying insecticidal compounds. For example it may be applied, formulated or unformulated, to the insect or to the locus of the insect (such as habitat of the insects, or a growing plant liable to infestation by the insects) or to the parts of the plants, including for example foliage, stems, branches or roots, to the seed before it is planted or to other media in which plants are growing or are to be planted (such as soil surrounding the roots or the soil generally) directly or it may be sprayed on, dusted on, applied by dipping, or applied through distribution or incorporation of a composition in soil or an aqueous environment.

The compounds of the present invention may also be injected into plants or sprayed onto plants using electrodynamic spraying techniques, or applied by land or aerial irrigation systems.

In an embodiment of the invention, the combination is applied during the phonological stage of tree, or as a prevention step before the phonological stage. In an embodiment of the invention, the timing for the application depends upon the life cycle of the insect.

In an embodiment of the invention the composition comprises a carrier or diluent (e.g. liquid, solid or semisolid carrier). The compositions may include excipients and/or additives (e.g. surface active agents, an oil, or any combination thereof).

According to a specific embodiment of the present invention, the carrier or diluent is an aqueous carrier.

In an embodiment of the invention the combination of compounds are administered in a composition further comprising excipients and/or additives.

In an embodiment of the invention, the additive comprising an oil. In certain embodiments the additive is an oil. The oil may be selected from mineral oil, vegetable oil, and mixtures thereof.

The concentration of the additive in the diluted composition (i.e. ready to use composition) may be for example 0.001% w/v and above, 0.01% w/v and above, 0.02% w/v and above, 0.05% w/v and above, 0.1% w/v and above.

The concentration of the additive in the diluted composition may be for example 3% w/v and below, 2% w/v and below, 1% w/v and below, 0.8% w/v and below, 0.6% w/v and below, 0.4% w/v and below, 0.3% w/v and below.

The concentration may be any intermediate concentration formed by combining the above concentrations, for example the concentration of the additive may be in the range 0.001 to 3% w/v, 0.01 to 3% w/v, 0.01 to 2% w/v, 0.02 to 2% w/v, 0.05 to 2% w/v, etc.

The weight ratio of the combination of the neonicotinoid compound and the BPU compound to the additive may be for example in the range 1000:1 to 1:1000, 400:1 to 1:400, 100:1 to 1:400, 20:1 to 1:400, 15:1 to 1:300, 10:1 to 1:100, 5:1 to 1:50, or 1:1 to 1:40.

As used herein the term "weight ratio of the combination of the neonicotinoid compound and the BPU compound to the additive" refers to the weight ratio of the total weight of the combination of compounds (i.e. the neonicitinoid compound and the BPU compound) to the weight of the additive.

The above ratios refer to the ready to use compositions.

The oil (e.g. mineral oil or vegetable oil) may possess an insect control activity and/or may facilitate spreading of the compounds at the site of application.

The invention additionally relates to a composition comprising a combination of at least one neonicotinoid compound and at least one benzoylphenyl urea (BPU) compound, for use as insect control agent, wherein the insect is woolly apple aphid.

The invention additionally relates to a composition comprising a combination of at least one neonicotinoid compound and at least one benzoylphenyl urea (BPU) compound, for controlling woolly apple aphid.

The invention further relates to use of a combination of at least one neonicotinoid compound and at least one benzoylphenyl urea (BPU) compound as an insect control agent, wherein the insect is woolly apple aphid.

The invention further relates to use of a combination of at least one neonicotinoid compound and at least one benzoylphenyl urea (BPU) compound for controlling woolly apple aphid.

According to a specific embodiment the insect control is for use in plant protection.

Additionally, the invention relates to a kit comprising (a) at least one container including at least one neonicotinoid compound; (b) at least one container including at least one benzoylphenyl urea compound; and instructions for applying a combination of the neonicotinoid compound and the benzoylphenyl urea compound onto woolly apple aphid insect or a locus where control of the insect is desired.

In an embodiment of the invention, the neonicotinoid compound and the benzoylphenyl urea compound are applied concomitantly or sequentially.

Moreover, the invention relates to a kit comprising at least one container including a combination of at least one neonicotinoid compound and at least one benzoylphenyl urea compound, and instructions for applying the combination onto woolly apple aphid insect or a locus where control of the insect is desired.

The instructions may be in the form of printed matter, for example either as inserts or labels.

It is appreciated that one or more features, aspects, or embodiments of the present invention can be combined with one or more other features, aspects or embodiments of the present invention.

It is recognized that all embodiments of the invention, including those specifically described for different aspects of the invention, can be combined with any other embodiments of the invention as appropriate.

It is appreciated that the neonicotinoid and benzoylphenyl urea compounds, described in the invention in a particular aspect may be characterized by the various features, compositions, rates of applications etc. described in the present invention in the other aspects.

While embodiments of the invention have been described by way of illustration, it will be apparent that the invention may be carried out with many modifications, variations and adaptations, without departing from its spirit or exceeding the scope of the claims.

In order to understand the invention and to see how it may be carried-out in practice, the following examples are described showing the effects of different concentrations of novaluron or acetamipirid or combinations thereof in controlling woolly apple aphid in apple trees.

EXAMPLES

Experimental Procedures

Purpose

The purpose of the experiments was to evaluate the efficacy of mixtures in various concentrations of insecticides, in the control of woolly apple aphid (*Eriosoma lanigerum*) in apple trees found at different locations.

Materials

Rimon 10 EC (Novaluron 100 g/l, tradename: Rimon 10 EC, manufactured by Makhteshim Chemical works, Israel), Ac 20 SP (Acetamiprid 20%, soluble powder formulation, in-house laboratory scale preparation); and Seizer 10 EC (Bifenthrin 100 g/l, tradename: Seizer 10 EC, manufactured by Makhteshim Chemical Works, Israel). EOS (mineral oil 99%, tradename: EOS, Makhteshim Chemical Works, Israel). A soluble powder formulation of acetamiprid is commercially available, e.g., under the tradename Mospilan 20 SP, Nippon Soda Co. Ltd. Japan.

Methodology

The essay was conducted in orchards suffering from woolly apple aphid (Eriosoma lanigerum) insect, in the following locations: 1) La Pintana, Santiago, 2) Codegua, Rancagua, O'Higgins Region and 3) Los Niches, Curicó, Maule Region, in Chile.

During the appropriate season, three applications were conducted, at 22 day interval, in each orchard, applying a water volume of 2000 L/ha.

Essay Design

A random full-block design was used, with four repetitions separated from each other by two trees. The sample unit corresponds to 10 trees. For the evaluations, a number of samples equal to n=100, i.e. 25 twigs of each unit was used.

The treatments used in the essay are shown below, in Table 1.

TABLE 1

Details of treatments, active ingredients and concentration used

| Treatment | Product Formulation | Ingredients | Concentration in 100 L water |
|---|---|---|---|
| 1 | Rimon 10 EC* | Novaluron | 50.0 cc |
|  | Ac 20 SP# | Acetamiprid | 12.5 g |
|  | EOS*** | Mineral oil | 200.0 cc |
| 2 | Rimon 10 EC | Novaluron | 75.0 cc |
|  | Ac 20 SP | Acetamiprid | 12.5 g |
|  | EOS | Mineral oil | 200.00 cc |
| 3 | Rimon 10 EC | Novaluron | 100.0 cc |
|  | Ac 20 SP | Acetamiprid | 12.5 g |
|  | EOS | Mineral oil | 200.00 cc |
| 4 | Rimon 10 EC | Novaluron | 50.0 cc |
|  | Ac 20 SP | Acetamiprid | 20.0 g |
|  | EOS | Mineral oil | 200.00 cc |
| 5 | Rimon 10 EC | Novaluron | 75.0 cc |
|  | Ac 20 SP | Acetamiprid | 20.0 g |
|  | EOS | Mineral oil | 200.0 cc |
| 6 | Rimon 10 EC | Novaluron | 100.0 cc |
|  | Ac 20 SP | Acetamiprid | 20.0 g |
|  | EOS | Mineral oil | 200.0 cc |
| 7 | Ac 20 SP | Acetamiprid | 12.5 g |
|  | EOS | Mineral oil | 200.0 cc |
| 8 | Ac 20 SP | Acetamiprid | 20.0 g |
|  | EOS | Mineral oil | 200.0 cc |
| 9 | Rimon 10 EC | Novaluron | 50.0 g |
|  | EOS | Mineral oil | 200.0 cc |
| 10 | Rimon 10 EC | Novaluron | 75.0 cc |
|  | EOS | Mineral oil | 200.0 cc |
| 11 | Rimon 10 EC | Novaluron | 100.0 cc |
|  | EOS | Mineral oil | 200.0 cc |
| 12 | Control[A] |  |  |
| 13 | Seizer 10 EC ** | Bifenthrin | 8.0 cc |
|  | Ac 20 SP | Acetamiprid | 40.0 g |
|  | EOS | Mineral oil | 200.0 cc |
| 14 | Seizer 10 EC | Bifenthrin | 12.0 cc |
|  | Ac 20 SP | Acetapirimid | 40.0 g |
|  | EOS | Mineral oil | 200.0 cc |

*Rimon 10 EC contains 100 g of the active ingredient (Novaluron) in one liter [emulsifiable concentrate formulation].
Ac 20 SP contains 200 g of the active ingredient (Acetamiprid) in 1000 g [soluble powder formulation].
** Seizer 10 EC contains 100 g of the active ingredient (Bifenthrin) in one liter [emulsifiable concentrate formulation].
*** EOS (99% mineral oil, , 1% of a surfactant (ethoxylated Lauryl Amine)).
[A]The Control (treatment 12) was untreated tree.

Preparation

The treatments in the trial were applied using barrel hand gun sprayer. Spray dilutions were made filling the barrel by half with water, then adding the required amount of product while agitating, adding additional water and topping with the required amount of oil (EOS). An identical amount of EOS was used in each treatment.

Evaluation

Below are the dates of application and evaluation in the three locations.

TABLE 2

Dates of the activities conducted for the essay by region.

| Event | Metropolitan Region, La Pintana | O'Higgins Region, Codegua | Maule Region, Los Niches |
|---|---|---|---|
| Application 1 | November 8 | November 8 | November 7 |
| First evaluation (DDA 19) | November 27 | November 27 | November 26 |
| Application 2 | November 30 | November 30 | November 29 |
| Second evaluation (DDA 21) | December 21 | December 21 | December 20 |
| Application 3 | December 22 | December 22 | December 21 |
| Third evaluation (DDA 18) | January 9 | January 9 | January 8 |
| Fourth evaluation (DDA 23) | January 14 | January 14 | January 13 |

The evaluations of woolly apple aphid were conducted on twigs of 10 to 15 cm, determining under stereoscopic lens the condition of the individuals present, to discard those twigs that only show aphids with parasites.

Statistical Analysis

A variance homogeneity test was conducted prior to the ANOVA, for which reason statistical transformations were used only when necessary. Then, the Tukey comparison test was conducted to establish differences in the results of the treatments (p=0.05) by using the statistical software SSPS 14.0 for Windows.

Experimental Results

Below are tables with the average of repetitions for each treatment together with the number of twigs infested by woolly apple aphid (Eriosoma lanigerum) in each of the locations specified above.

TABLE 3

Average twigs infested by woolly apple aphid in the essay evaluations (n = 100)
METROPOLITAN REGION

| Treatment | Average number of twigs infested by woolly apple aphid | | | |
|---|---|---|---|---|
|  | 1st evaluation | 2nd evaluation | 3rd evaluation | 4th evaluation |
| T1 | 25.0 fghi | 22.5 efg | 26.0 g | 24.0 fg |
| T2 | 21.0 cde | 20.0 cde | 22.5 efg | 22.0 efg |
| T3 | 22.0 def | 21.0 def | 24.0 fg | 20.0 def |
| T4 | 19.0 bcd | 17.0 bc | 15.0 bc | 12.8 bc |
| T5 | 17.0 ab | 15.0 ab | 12.8 ab | 9.0 ab |
| T6 | 15.0 a | 13.0 a | 10.0 a | 6.0 a |
| T7 | 29.0 j | 24.0 fgh | 21.0 def | 25.0 g |
| T8 | 24.0 efgh | 22.0 defg | 20.0 def | 19.0 de |
| T9 | 27.0 hij | 25.0 gh | 22.0 efg | 21.0 defg |
| T10 | 23.0 efg | 20.0 cde | 19.0 cde | 17.0 cd |
| T11 | 18.0 abc | 19.0 cd | 11.0 bcd | 18.0 de |
| T12 | 33.8 k | 35.3 i | 36.3 h | 37.5 h |
| T13 | 28.0 ij | 27.0 h | 24.0 fg | 20.0 def |
| T14 | 26.0 ghij | 25.0 gh | 20.0 def | 21.0 defg |

The entries in the table followed by identical letters do not show any significant statistical difference at p=0.05 level.

TABLE 4

Average twigs infested with woolly apple aphid in essay evaluations (n = 100)
O'HIGGINS REGION Average number of twigs infested by woolly apple aphid

| Treatment | 1st evaluation | 2nd evaluation | 3rd evaluation | 4th evaluation |
|---|---|---|---|---|
| T1 | 26.5 ghi | 24.5 fg | 27.0 f | 26.0 fg |
| T2 | 23.0 defg | 26.5 g | 25.0 def | 28.0 g |
| T3 | 25.0 fgh | 22.5 def | 20.8 bcd | 19.0 c |
| T4 | 21.0 cde | 20.0 bcd | 17.0 b | 14.0 b |
| T5 | 19.0 bc | 11.0 a | 9.0 a | 7.0 a |
| T6 | 13.0 a | 9.0 a | 7.0 a | 11.0 b |
| T7 | 23.0 defg | 21.0 bcde | 24.0 cdef | 20.0 cd |
| T8 | 20.0 bcd | 19.0 bc | 22.0 cde | 21.0 cde |
| T9 | 24.0 fghi | 22.0 cdef | 20.0 bc | 23.0 def |
| T10 | 22.0 cdef | 21.0 bcde | 22.5 cde | 24.0 ef |
| T11 | 17.0 b | 18.0 b | 21.0 bcd | 19.0 c |
| T12 | 33.8 j | 34.8 h | 35.8 g | 37.8 h |
| T13 | 29.0 i | 24.0 efg | 26.0 ef | 22.0 cde |
| T14 | 27.0 hi | 26.0 g | 24.0 cdef | 20.0 cd |

The entries in the table followed by identical letters do not show any significant statistical difference at p=0.05 level.

TABLE 5

Average twigs infested with woolly apple aphid in essay evaluations (n = 100)
MAULE REGION Average number of twigs infested with woolly apple aphid

| Treatment | 1st evaluation | 2nd evaluation | 3rd evaluation | 4th evaluation |
|---|---|---|---|---|
| T1 | 30.0 f | 27.0 fgh | 24.0 efg | 25.0 ef |
| T2 | 27.0 ef | 29.0 hi | 26.0 fg | 27.0 f |
| T3 | 24.0 cde | 26.0 efg | 22.5 efg | 21.0 cde |
| T4 | 22.0 bcde | 19.0 b | 16.0 bcd | 12.0 ab |
| T5 | 15.5 a | 13.0 a | 10.0 a | 11.0 a |
| T6 | 18.0 ab | 15.0 a | 12.0 ab | 9.0 a |
| T7 | 20.0 abc | 23.0 cd | 19.0 cde | 24.0 ef |
| T8 | 23.0 bcde | 20.0 b | 17.0 bcd | 18.0 cd |
| T9 | 25.0 cdef | 21.0 bc | 22.0 defg | 20.0 cde |
| T10 | 24.0 cde | 25.0 def | 25.5 fg | 23.0 def |
| T11 | 21.0 bcd | 19.0 b | 20.0 cde | 17.0 bc |
| T12 | 29.3 f | 31.0 i | 32.5 h | 35.0 g |
| T13 | 26.0 def | 28.0 gh | 27.0 g | 24.0 ef |
| T14 | 23.0 bcde | 24.0 de | 21.0 cdef | 22.0 cdef |

The entries in the table followed by identical letters do not show any significant statistical difference at p=0.05 level.

CONCLUSIONS

As can be clearly seen from tables Nos. 3, 4 and 5, the combination of Rimon 10 EC (Novaluron) and Ac 20 SP (Acetamiprid) (+mineral oil) was most effective in controlling the woolly apple aphid. In particular, treatments 5 and 6 (Table 1) were most efficient in controlling the woolly apple aphid. In contrast, the treatment of acetamipirid (+mineral oil) alone or the treatment of novaluron (+mineral oil) alone was not effective in controlling the woolly apple aphid.

While this invention has been shown and described with reference to preferred embodiments thereof, it will be understood by those skilled in the art that many alternatives, modifications and variations may be made thereto without departing from the spirit and scope of the invention. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference.

What is claimed is:

1. A method for controlling woolly apple aphid insect comprising contacting the insect or a locus, where control of the insect is desired, with a combination comprising 0.004 percent by weight acetamiprid and 0.005 to 0.01 percent by weight novaluron.

2. The method of claim 1, wherein said locus is one or both of a plant and its environment.

3. The method of claim 2, wherein said plant is a fruit tree.

4. The method of claim 3, wherein said fruit tree is selected from an apple tree, an elm tree, a pear tree, a quince tree, a hawthorn tree, a mountain ash tree, and cotoneaster tree.

5. The method of claim 1, wherein said acetamiprid and said novaluron are administered sequentially or simultaneously.

6. The method of claim 1 wherein said acetamiprid and said novaluron are administered within a time difference of not more than 14 days.

7. The method of claim 1, wherein said acetamiprid and said novaluron are applied in a single composition or separate compositions comprising thereof.

8. The method of claim 1, wherein said combination is administered in a composition further comprising excipients and/or additives.

9. The method of claim 8, wherein the additive comprises an oil selected from mineral oil, vegetable oil, and mixtures thereof.

10. The method according to claim 3, wherein when applied to fruit trees, the acetamiprid is applied at a rate of 20 g/hectare to 500 g/hectare and novaluron is applied at a rate of 20 g/hectare to 500 g/hectare.

* * * * *